(12) United States Patent
Nash et al.

(10) Patent No.: US 7,972,294 B2
(45) Date of Patent: *Jul. 5, 2011

(54) CATHETER WITH ASSOCIATED EXTENSION LUMEN

(75) Inventors: John E. Nash, Chester Springs, PA (US); Gregory Walters, Malvern, PA (US)

(73) Assignee: Kensey Nash Corporation, Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/971,059

(22) Filed: Jan. 8, 2008

(65) Prior Publication Data

US 2008/0108946 A1     May 8, 2008

Related U.S. Application Data

(62) Division of application No. 10/401,407, filed on Mar. 28, 2003, now Pat. No. 7,316,678.

(51) Int. Cl.
*A61M 3/02* (2006.01)
(52) U.S. Cl. .......................................... 604/40; 604/523
(58) Field of Classification Search ................ 600/433; 604/40, 96.01, 523, 164.01–170.03, 524–532
See application file for complete search history.

(56) References Cited

U.S. PATENT DOCUMENTS

| | | | |
|---|---|---|---|
| 4,406,656 A * | 9/1983 | Hattler et al. ................. | 604/523 |
| 4,568,329 A | 2/1986 | Mahurkar | |
| 4,911,163 A * | 3/1990 | Fina .............................. | 606/127 |
| 5,195,962 A | 3/1993 | Martin et al. | |
| 5,207,648 A * | 5/1993 | Gross ....................... | 604/164.09 |
| 5,419,774 A | 5/1995 | Willard et al. | |
| 5,591,194 A * | 1/1997 | Berthiaume .................. | 606/192 |
| 5,728,065 A * | 3/1998 | Follmer et al. ............. | 604/96.01 |
| 5,833,644 A * | 11/1998 | Zadno-Azizi et al. ......... | 604/509 |
| 5,868,702 A * | 2/1999 | Stevens et al. ............. | 604/96.01 |
| 6,022,336 A | 2/2000 | Zadno-Azizi et al. | |
| 6,152,909 A | 11/2000 | Bagaoisan et al. | |
| 6,568,329 B1 | 5/2003 | Robinson | |
| 6,685,648 B2 | 2/2004 | Flaherty et al. | |
| 6,758,836 B2 * | 7/2004 | Zawacki ....................... | 604/284 |
| 7,063,714 B2 * | 6/2006 | Dorros et al. ................ | 606/194 |
| 2002/0091407 A1 * | 7/2002 | Zadno-Azizi et al. ........ | 606/200 |

* cited by examiner

*Primary Examiner* — Nicholas D Lucchesi
*Assistant Examiner* — Gerald Landry, II
(74) *Attorney, Agent, or Firm* — Jeffrey R. Ramberg

(57) ABSTRACT

An intra-luminal device for the extraction of occlusive or partially occlusive material is disclosed. The device includes a novel catheter extension which minimizes cavitation of extracted fluids and also allows the better navigation of tortuous lumens or vasculature.

28 Claims, 8 Drawing Sheets

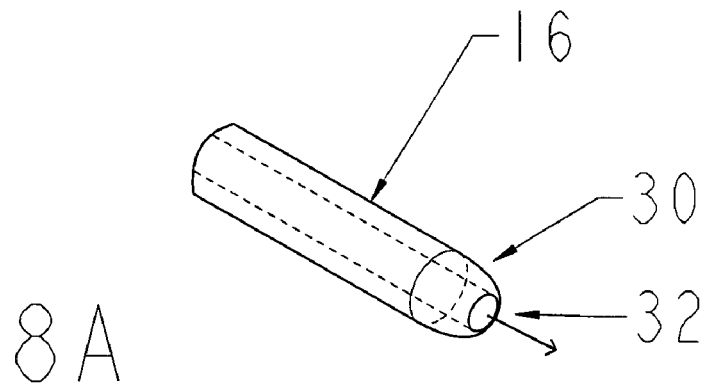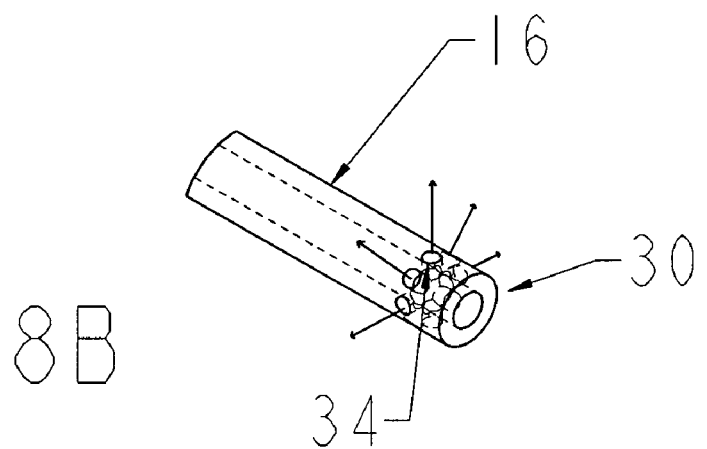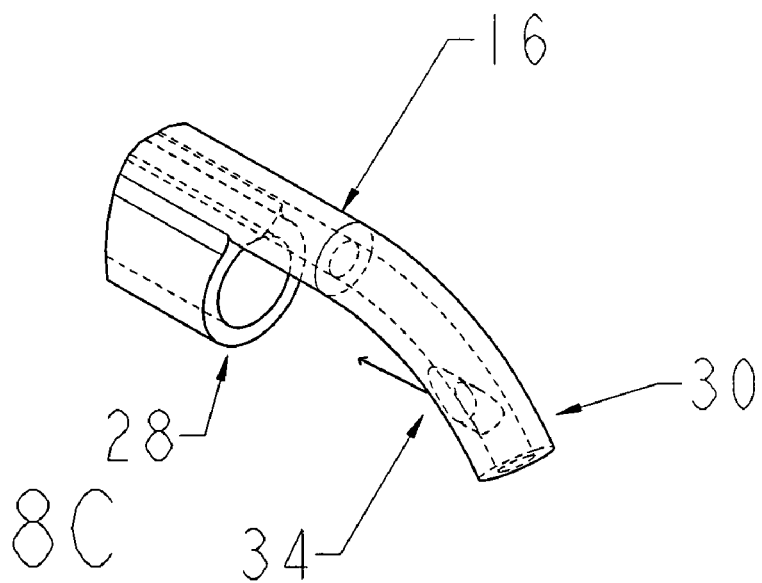

CATHETER WITH ASSOCIATED EXTENSION LUMEN

CROSS REFERENCE TO RELATED APPLICATIONS

This application is a divisional of U.S. patent application Ser. No. 10/401,407, filed Mar. 28, 2003 now U.S. Pat. No. 7,316,678, which is assigned to the same assignee as this invention and whose disclosure is fully incorporated by reference herein.

BACKGROUND OF THE INVENTION

The use of aspiration catheters for a variety of medical procedures has been well established, including the use of aspiration catheters for removing blood, obstructions, thrombus, or debris from blood vessels. This can be accomplished using manual means, like a hand pump or syringe, or mechanical means such as mechanical pump. Aspiration catheters have taken the form of simple single-lumen catheters or more complicated multi-lumen catheters. Perhaps the most common aspirations performed in blood vessels are those involving aspirations of thrombus through single lumen tubes that are opened to atmospheric pressure. These aspirations are commonly performed during surgery, or done percutaneously during coronary or peripheral interventions.

One problem common to all aspiration catheters is the natural tendency of the viscous blood to resist flow in channels, especially when these channels are small and long as they are with typical catheters, see e.g., U.S. Pat. No. 6,152,909 (Bagaoisan et al.). This resistance is termed 'viscous loss' and higher viscosity fluids or longer catheters require higher pressures to maintain sufficient flow, see e.g., U.S. Pat. Nos. 5,833,644 and 6,022,336 (Zadno-Azizi et al.). This becomes a difficult challenge when using aspiration catheters inside blood vessels since the pressure differential available to move the blood is never greater than atmospheric pressure and is often quite lower. Therefore, optimizing the channel size or ID of the catheter while maintaining a small OD of the catheter becomes a primary design requirement. Given the physical constraints of this problem, effective aspiration catheters are limited to ID's approximating 1 mm or larger for catheters longer than 100 cm. Hemodialysis catheters readily overcome this problem with large ID's, however these catheters are very short, see e.g. U.S. Pat. No. 6,568,329 (Mahurkar) and U.S. Pat. No. 5,195,962 (Martin et al.). Longer lengths of this catheter design would not function in an intra-thoracic procedure.

Another problem common to blood vessel catheters is maneuverability. That is, the ability for the catheter to be advanced into small tortuous vessels with ease. This requires small catheter diameters (and flexible materials), which is directly at odds with optimizing aspiration flow. In aspiration catheter constructions that involve additional functions beyond simple aspiration and thus require multiple lumens, this is especially problematic.

An aspiration catheter that is capable of being advanced into distal locations and directed beyond multiple branch points in the vasculature while being capable of suitable aspiration volumes would be desired.

SUMMARY OF THE INVENTION

The various embodiments of the present invention overcome these noted shortcomings of the art (e.g., cavitation in long catheters, and navigability of tortuous vasculature), as well as other shortcomings. The various exemplary embodiments providing these advantages follow.

A preferred embodiment of the present invention comprises a system for accessing lumens or other vasculature in living beings for the facilitation of intraluminal or other medical procedures, with the system basically comprising a first catheter, a catheter extension, and a control/locating member. The first catheter has a proximal end and a distal end with a channel therebetween; and the catheter extension comprises a proximal end and a distal end with an extension channel therebetween. The first catheter may be arranged to slidably and telescopically accept the catheter extension in said channel with said catheter extension thereby creating an overlapping segment between the catheters. The telescoping of the catheters will cause said channel and said extension channel to operate together to form a contiguous channel.

The control member has a proximal and a distal end with an elongate body arranged therebetween, and the control member may be attached to the catheter extension (e.g., at the proximal end, or along the side) and the elongate body extending through the channel in said first catheter at least to the proximal end of said extension catheter. In this arrangement the control member will cause the catheter extension to be at least partially expelled from said channel, or rotated in said channel, in said first catheter upon the application of a pushing force. Likewise, a pulling force would cause the retraction of the extension catheter into the lumen.

It is anticipated that the preferred embodiment will include an extension catheter having a length that is less than that of said first catheter, although this dimension is not critical. The overlap region may affect the amount of liquid drawn in (i.e., leaked) to the channel from the lumen, during use. The degree of the fit between the outside of the extension catheter and the inside of the first catheter will also be a key factor. This design contemplates and tolerates some leakage at this overlap region; however it is also recognized that an element (e.g., a bushing, washer, or flange) may be used to decrease this effect.

A preferred embodiment of this disclosure contemplates tubular catheters of round cross section, but other cross sectional geometries may be beneficial (e.g., to aid in steering or flexibility). Additionally, embodiments may comprise catheters (either primary or first catheters as well as extension catheters) which have decreasing diameters toward the distal end. These decreasing outside diameters may be accompanied by decreasing channel diameters, or the channels may remain constant.

In a preferred embodiment, the elongate body comprises a guide-wire passageway arranged between its proximal and distal ends to slidably accept a guide-wire. This guide-wire may also have a distal protection balloon or filter. Alternatively, the guide-wire may travel through the contiguous channel in the first catheter and the extension catheter.

A mixed-mode guide-wire arrangement may also be employed where the guide-wire runs through a portion of the channel, and enters a guide-wire passageway at some interface; with the interface being in the first catheter or the extension catheter.

In a preferred embodiment the elongate body comprises a fluid passageway arranged between its proximal and distal ends, with said fluid passageway arranged to infuse a liquid (e.g., saline, contrast media, drugs, biologically active agents, or any combinations thereof) at said distal end of said elongate body. This fluid passageway may also be employed with a guide-wire passageway (e.g., the previously discussed embodiment).

A preferred embodiment also utilizes a vacuum source (e.g., syringe or pump) attached to the contiguous channel to remove liquid (e.g., infusate and blood or other bodily fluid) together with any debris (e.g., atherosclerotic plaque, thrombus, tissue, or any combination thereof) which may be created during said procedure.

The various embodiments herein comprising infusion and extraction contemplate infusion rates or volumes higher or lower than aspiration rates. It is recognized that an extraction rate higher than an infusion rate should yield in the removal of blood from the body. This may also afford some additional protection from emboli or other debris, as the removal of additional fluid should cause the clearing the procedural area and proximate areas of debris.

The introduction of infusate may be performed at high pressure which may be caused by small orifices in the extension catheter, whereby the infusate causes liquid jets to be directed from the extension catheter. These jets may be directed proximally, distally, or radially outward, or any combination thereof. Proximal jets may also assist the entry of debris into any aspiration opening in the device.

BRIEF DESCRIPTION OF THE DRAWINGS

FIGS. 1,2,3a, 4a, 5a, 6a, 7a, and 8a-8c are isometric schematic views of various embodiments of the assembly of the present invention.

DETAILED DESCRIPTION

Figure 1:
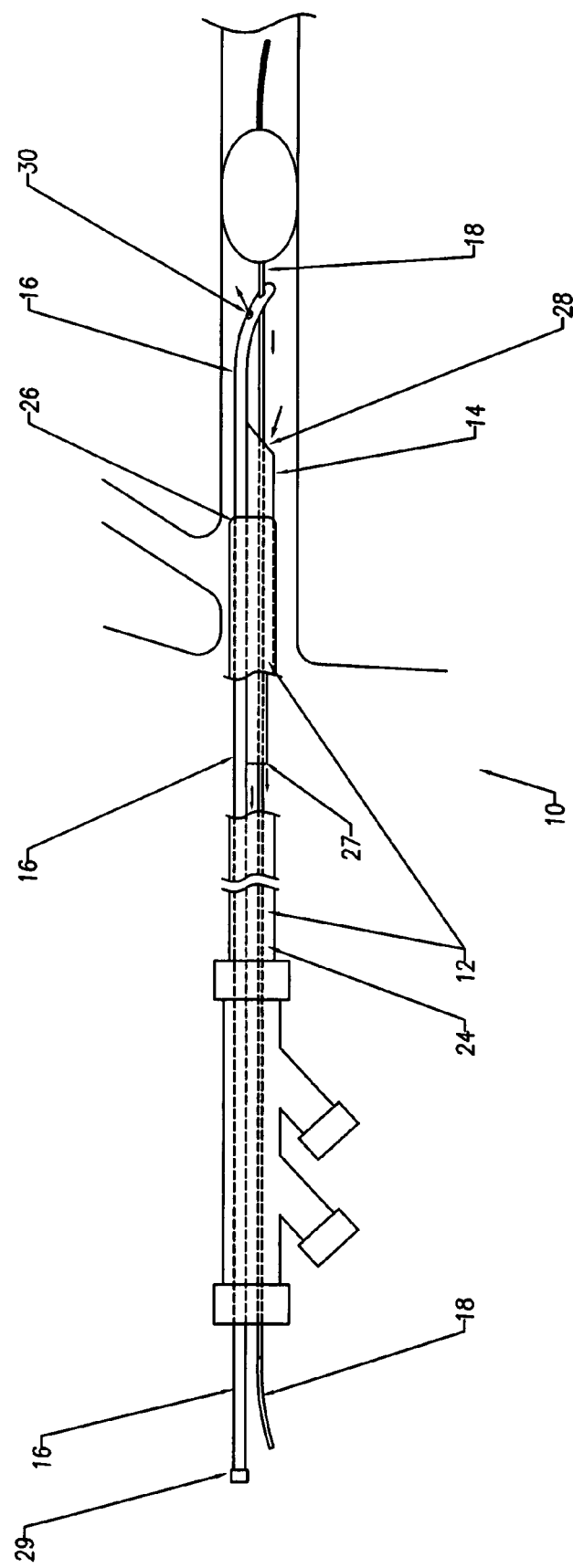

It is among the objects of the present invention to facilitate intravascular or intra-luminal procedures, especially the clearing of an occluded lumen by, in various preferred embodiments, providing a device for use in delivering infusion/irrigation to the lumen, causing extraction of any debris, and providing distal protection necessary for the procedure.

Various embodiments will include, among other things, an infusate fluid pathway, and an extraction pathway, pumping means, distal protection means, guidewires, a primary or guide catheter, a catheter extension, and a locating member, various arrangements of these components are discussed below.

Extraction Pathway

The invention overcomes the drawbacks of the prior art including, but not limited to, the incorporation of measures necessary to reduce the occurrence of cavitation within the extraction pathway of the device. The invention is such that it has the ability to efficiently withdraw fluid and debris from the body via the extraction pathway, with low pressure drop and without incurring cavitation. Contrasted with the prior art, wherein fluid and debris may be extracted, however the extraction rate is necessarily much lower due to the nature of the prior art embodiments being more susceptible to cavitation than is the present invention. The prior designs have traditionally been of a 'lumen within a lumen' design, or alternatively 'side by side' lumens extending substantially equal lengths and either forming concentric walls or adjacent walls with spaces between serving as the infusion and extraction pathways. The presence of these walls has the effect of limiting or occluding the extraction pathway, and as a result, in order to avoid cavitation with the prior art devices, extraction vacuum must be lower and exerted over a longer period of time in order to perform the extraction procedure, as due to the viscous nature of the fluids, they must move at a very low rate in order to avoid cavitation from occurring within the long narrow channels. As described herein, the subject invention attempts to maximize the diameter of the extraction pathway, and where the extraction pathway must be smaller to reach further into the body, the narrower portion is kept shorter in length, possibly much shorter in length than the entire extraction pathway, and situated distally from a vacuum source.

The extraction pathway is driven by a vacuum created by the vacuum source, such as any aspiration pump known in the art. The vacuum source is preferably located near the body while undergoing the procedure, but may be located remotely from the body as well. The vacuum source is operatively connected to the inside channel of a first catheter. The first catheter encompasses a channel with a proximal and distal end, and is typical of catheters known in the art. In use, the first catheter extends distally towards and into the living body, while the proximal end of the first catheter remains in operative contact to the vacuum source. The proximal end of the first catheter is of a size suitable for insertion into the living body and directed towards the affected or occluded lumen of the living being by traveling into the vasculature of the living being via an access point, typically from an incision or puncture into an artery located in the thigh; however, access may be gained at any location known to the art.

In order to reach more tortuous vasculature, a catheter extension is provided, and in use is operatively received in the first catheter. The outside diameter of the catheter extension must be such that it may fit within the inside diameter of the first catheter. In this manner the channel of the catheter extension is operatively connected to the channel of the first catheter, forming a contiguous channel or pathway. Additionally, the catheter extension is capable of being movably or slidably operated in the first catheter. Thus, there is an overlapping region where at least a portion of the channel of the catheter extension is located within the channel of the first catheter. The extent or length of this overlapping region or segment will vary in accordance with the extent that the catheter extension is extended from, or retracted back into the first catheter. The catheter extension may be directed into place by a location member or a control member, which is operatively connected to at least a portion of the catheter extension at or near the distal end of the control member. In use, the proximal end of the control member is arranged to extend out of the body, enabling the user to exert a force on the control member, for example, the control member may be pushed, pulled, or twisted depending on the steering needs for the catheter extension. The pushing, pulling and twisting forces exerted upon the control member will direct the catheter extension in extension, retraction, and rotation, respectively, relative to the distal end of the first catheter.

In use, at least the proximal end of the catheter extension is maintained within the channel of the first catheter, and the catheter extension maybe extended outward distally from the distal end of the catheter. The design and construction of the catheter extension enables it to extend further into the vasculature than the first catheter, by navigating more tortuous bends and smaller diameter vessels to reach the affected or occluded area of a lumen or vessel (i.e., a blood vessel). This is at least partially due to the smaller outside diameter of the catheter extension (relative to the first catheter), but it may also be due to the construction or the geometry of the catheter extension, as will be discussed later.

The vacuum source is capable of drawing into the catheter extension any debris released into the area during the procedure, together with any infusate. The debris released may include atherosclerotic plaque, thrombus, tissue or any combination thereof. In use, the debris is drawn by vacuum into the distal opening of the catheter extension, and then drawn through the length of the channel of the catheter extension, and into the channel formed by the larger bore of the first catheter, and ultimately to a collection point located outside the body such as a debris trap or collection bag associated with the vacuum source.

The vacuum applied must be capable of drawing debris and sufficient volume from a distance (i.e., at least one, but more typically two or more meters) through a narrow catheter suitably sized for use in the vasculature of a living being. For these reasons, a relatively strong vacuum, aspiration or extraction pump is required. Vacuum levels often are at least 300 mm Hg, occasionally as high as 700-760 mm Hg. Given the level of the vacuum required, there is a concern of cavitation, the occurrence of bubbles, within the extraction pathway created by the vacuum. If bubbles are produced, the volume of fluid in the removal channel increases and the rate of debris removal may be drastically decreased.

The fluid dynamics in an arrangement described above are such that the highest vacuum levels would be found closest to the vacuum source (towards the proximal end of the extraction pathway), with the vacuum levels diminishing further away from the source (towards the distal end of the extraction pathway). This effect is due mainly to the viscosity of the fluid in contact with the perimeter of fluid bore. For these reasons, vacuum levels decrease the further the point is from the vacuum source.

Once the fluid and debris is drawn by the vacuum source, from the relatively narrow catheter extension channel into the relatively larger channel of the first catheter, cavitation is less likely in the larger inner diameter of the first catheter channel. This reduced cavitation is due to the lessened frictional effects due to the larger inner diameter of the first catheter channel, relative to the smaller bored catheter extension channel. The fluid in the larger bore will experience less drag and can offer greater flow yet at a slower velocity.

Infusate Fluid Pathway

The subject invention is also designed to flush or infuse the affected or occluded area of the vessel with an infusate fluid. The infusate may additionally be used as a means of delivering a drug or biologically active agent to the area. In an alternate embodiment, the infusate may be a saline solution being utilized to agitate or flush out any debris from the occluded area. In yet another embodiment, the infusate may be a contrast media, which would allow visualization of the procedure by any means known in the art, such as by fluoroscopy or MRI. A preferred embodiment may be a combination of a plurality of different infusate media, combining flushing properties along with drug or agent delivery properties within the same infusate fluid. Alternatively, during the procedure, different fluids may be infused, for example, a contrast media may be infused to visualize the area, followed by a saline solution to clear debris during the procedure, finally followed by a drug or beneficial agent delivered in a fluid, to treat the area. It is recognized that the infusate may be delivered at a rate equal to or different from the rate of extraction or aspiration of fluid via the extraction pathway. In a preferred embodiment, a rate of infusion is about 80% that of the rate of aspiration. In this manner, the removal of the debris is ensured, in order to minimize contaminating the blood stream with loose debris.

An infusion pump, preferably located near the living body undergoing the procedure, drives the infusate through the infusate pathway, however it is recognized that the infusion pump may be located away from the body as well, and the pressurized fluid delivered via a conduit. Instead of a pump arrangement, any pressurized system may be utilized to deliver the infusate fluid, e.g. pressure from compression upon a reservoir, or elevation may supply the required pressure. The infusion system must be capable of achieving pressures high enough to deliver the infusion fluid through a fluid passageway running at least the length of a contiguous channel comprising the channels of both the catheter and the catheter extension while in use. The fluid passageway may comprise an infusion lumen dedicated solely for delivery of infusate, or in another embodiment the fluid passageway may additionally serve as a lumen for a guidewire, to be discussed below.

The infusate fluid may exit the catheter extension in a gentle manner, to gently lavage the target area, or alternatively the infusate may exit in the form of higher velocity jets or streams to more effectively agitate and generate debris. In one possible embodiment, a single stream may exit the distal end of the fluid passageway, typically at or near the distal end of the catheter extension, as shown in FIG. 8a. As used in this application, the term "stream" encompasses a flow of liquid through an outlet, the flow may be in various forms, including but not limited to a fan spray, or a focused jet, either in a pulsating or steady manner. In an alternate embodiment, there may be a plurality of streams exiting the distal end of the fluid pathway, either directed radially outward from the central axis of the fluid pathway, as shown in FIG. 8b, or coaxially with the axis of the fluid pathway, or a combination of both orientations. Streams directed radially out from the fluid passageway directed towards the inner walls of the blood vessel may be useful to clear debris from the blood vessel wall. Streams directed coaxially in a distal orientation may be utilized to break up occlusions that are completely, or less than completely blocking the blood vessel and blood flow therethrough. As shown in FIG. 8c, any streams directed coaxially and in a proximal direction may be useful to break up debris, but primarily may be utilized to create a flow towards the extraction pathway via the catheter extension's distal end, thereby drawing in debris to be removed from the body. In a preferred embodiment, at least a portion of the infusate fluid stream may be directed toward the distal end of the catheter extension, in this manner drawing the generated debris into the extraction pathway, with the remainder of the infusate fluid directed as needed to agitate and remove debris, e.g., radially towards the inner wall of the blood vessel.

Depending upon the direction of fluid flow; that is, depending upon whether the overlapping segment is part of the extraction pathway, or part of the infusate pathway, one might suppose that there could be leakage of fluid either out of, or into, the assembly at this location, since the assembly during operation is maintained at a pressure that is above or below (e.g., vacuum) the pressure of the surrounding environment within the body of the being. To the extent that this is a concern, one may wish to incorporate a sealing means such as an elastomeric washer at this overlap segment, and in particular locating the sealing means between the outer wall of the catheter extension and the inner wall of the first catheter. On the other hand, the pressure or vacuum difference from inside to outside of the assembly at this point often is not that large. Further, the overlapping segment usually is sufficiently long and the gap between walls sufficiently small that the amount of leakage of fluid, either in or out, generally will be de minimus.

GW Arrangement Alternatives

It is recognized that the components comprising the invention may be assembled in several arrangements to achieve the desired embodiment of a catheter having a controllable catheter extension, the assembly being capable of infusing and aspirating fluid and debris.

Referring now to the various figures of the drawings, wherein like reference characters refer to like parts, there is shown a possible embodiment of the assembly 10, as it is to be used within the vasculature of the body. In this embodiment, the first catheter 12 is partially cut away in order to more clearly depict the catheter extension 14, and the catheter extension proximal end 27. In use, the catheter extension may be extended out from the first catheter 12 and controlled by the control member 16 upon application of a force applied at the control member proximal end 19, located outside the body. In this embodiment, a standard connector branch is shown affixed to the first catheter proximal end 24. Furthermore the control member 16 and a guidewire 18 extend through the connector branch into the first catheter 12, and through the length of the contiguous channel formed by the first catheter channel and the catheter extension channel (to be discussed later). In use the first catheter is extended into the vasculature of the body, and directed therethrough along the guidewire. The distal portion of the assembly is herein depicted having a control member with a distal end 30 wherein the guidewire 18 is slidably arranged therethrough. In this embodiment, the guidewire 18 is shown having a distal protection device, in this case a balloon is depicted, however other distal protection devices may be utilized.

Figure 2:
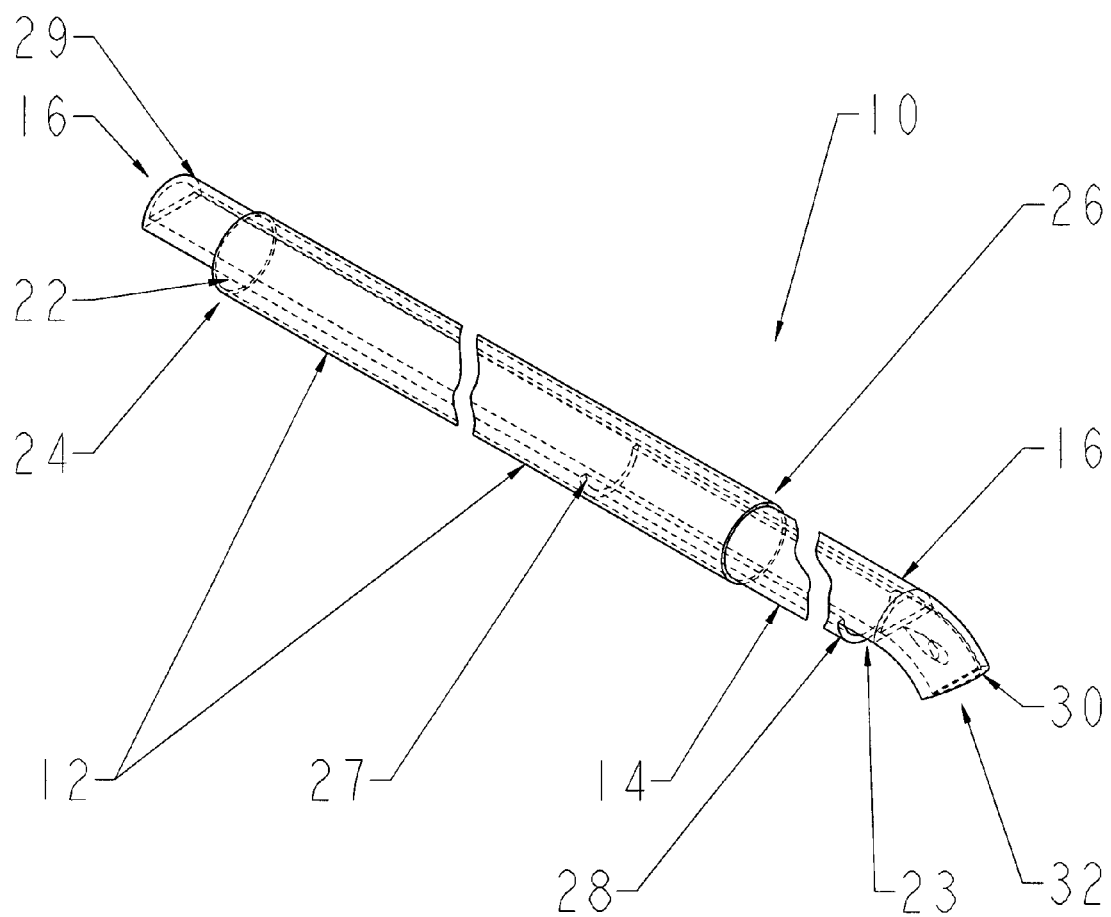

FIG. 2 depicts a possible embodiment of the assembly 10 of the present invention, wherein the assembly as shown may utilize a standard guidewire (not shown) as known in the art to facilitate the positioning of the assembly, however the assembly does not require the guidewire to be in place during use.

In embodiments where a guidewire is inside the device throughout its use, the guidewire may be initially directed to a place within the body undergoing the procedure. The assembly may then be inserted over the guide wire, or attached alongside the guide wire, using procedures known in the art, whereupon the assembly may be directed along the length of the guidewire, to arrive at or near the vasculature to be treated. The guidewire may then be removed from the body or partially withdrawn from the area before use. Alternatively, in some embodiments, the assembly incorporates the guidewire, wherein the guidewire may be left in place while the procedure is completed.

For the use of the embodiments wherein the guide wire is left in place during the procedure, the guidewire may incorporate the use of any suitable distal protection elements or devices known in the art, for example a balloon or an umbrella filter may be deployed distal to the area to be treated. These techniques serve to prevent any debris generated during the procedure from traveling throughout the vasculature, and potentially causing a stroke or embolism.

FIG. 2 depicts the assembly 10 as it would be used during a procedure within a body, with the guide wire having been removed. The first catheter 12 serves as the larger diameter lumen, and is capable of traveling into the vasculature along the larger arteries and blood vessels, but is limited in penetration by the diameter and reduced flexibility of the larger diameter of the first catheter 12. It is recognized that either or both the first catheter and the catheter extension may vary in size along its respective lengths. In a preferred embodiment (not shown), the catheter extension 14 will be of a larger overall diameter at the catheter extension's proximal end 27 and a smaller overall diameter at the catheter extension's distal end 28, reducing in overall diameter either gradually or in a punctuated manner. It is recognized that the reduction in diameter may be uniform over the length of the catheter extension 14 or limited to at least one portion of the catheter extension, in order to maximize strength and flexibility as required for specific needs. Similarly, the diameter of the catheter extension channel 23 may be larger at the catheter extension proximal end 27 than at the catheter extension distal end 28. In this manner, the increased flexibility required for the more vasculature regions is achieved, without decreasing the strength of the catheter extension.

The catheter extension 14 may be inserted into the body simultaneously with the insertion of the first catheter 12 over or alongside the guide wire (not shown). Alternatively and more preferably, the catheter extension 14 may be inserted into the first catheter channel 22 at the first catheter proximal end 24, and directed through the first catheter channel 22 towards the first catheter distal end 26 after the first catheter 12 is in place within the vasculature of the body. The insertion of the catheter extension 14 into the first catheter channel 22, and subsequently into the body, may be made after the complete removal or partial withdrawal of the guide wire.

The catheter extension 14 may be operatively controlled by a control member 16, which is connected to at least the catheter extension's proximal end 27. Alternatively, the control member 16 may be affixed along the entire length of the catheter extension 14. It is recognized the control member 16 may not extend distally beyond the catheter extension proximal end 27; alternatively, the control member 16 may extend as far as the catheter extension distal end 28; or alternatively, the control member 16 may extend distally beyond the catheter extension distal end 28 as shown in FIG. 2, as will be discussed. The control member's proximal end 29 extends proximally outside the body, thereby allowing the user access to the control member 16, in order to enable operative control, such that by pulling on the control member's proximal end 29, the catheter extension 14 may be retracted proximally toward and into the first catheter channel 22; conversely a pushing force exerted upon the control member's proximal end 29 may provide distal extension of the catheter extension 14 further into the vasculature, and out from the first catheter channel 22.

The control member 16 may be a strand, wire, filament or remaining wall section suitable for directing the movement of the catheter extension 14. The construction may be of any material suitable to resist compression and extension forces, as well as being capable of resisting torquing forces, such that the catheter extension 14 may be directed by twisting the control member proximal end 29. Additionally, and as depicted by the embodiment shown in FIG. 2, the control member 16 may also serve to deliver infusate liquid. Whether the control member is to be utilized to deliver infusate or not, it is recognized that the contiguous channel may be utilized as a lumen for bi-directional flow, varying the flow direction as needed by attaching either an aspiration means or infusion means to the connector branch or first catheter proximal end as required. In the embodiment having a control member capable of delivering infusate, the control member 16 may feature a lumen from the control member proximal end 29 to an opening or plurality of openings located at or near the control member distal end 30. The control member proximal end 29 may be operatively connected to a pressurized infusion system or to an outlet from an infusion pump (not shown). The connection (not shown) may be of any connection known in the art, including a threaded connection (i.e., a luer lock or screw type fitting), or a pressure fit connection (i.e., a touhy-bourst connector), or any suitable means to connect two lumens and allow pressurized flow of liquid therethrough.

The control member distal end 30 of an infusate delivering embodiment may have an end opening 32, wherein the pressurized infusate would flow straight out of the distal end 30. Alternatively, the control member distal end 30 may be shaped or curved to direct the flow of the infusate or to enable steering of the catheter extension. It is recognized that the control member distal end 30 may incorporate a unique head, adapted for distributing or dispensing the infusate, or alternatively may incorporate a floppy tip (not shown), as known in the art, the floppy tip serving to reduce damage to the vascular system in use, yet still be capable of delivery of infusate if required through openings.

In any of the embodiments wherein the control member is arranged to deliver infusate, the control member distal end 30 may have a single opening or a plurality of openings to allow the flow of infusate therethrough, as will be discussed. The infusate fluid may flow, under pressure maintained through the infusate pathway, through at least one opening at or near the control member distal end 30, into the area to be treated. The flow of fluid may be gentle, in order to wash the area to be treated, or alternatively, the flow may be at a velocity such that at least one jet may be formed. A jet or plurality of jets may serve to break up any occlusion or partial occlusion (e.g., thrombus, plaque, tissue, or clot) in the vessel by ablating or disrupting the occlusion. In this manner, an occlusion may be removed and free fluid flow through the vessel may be restored.

Figure 3A:
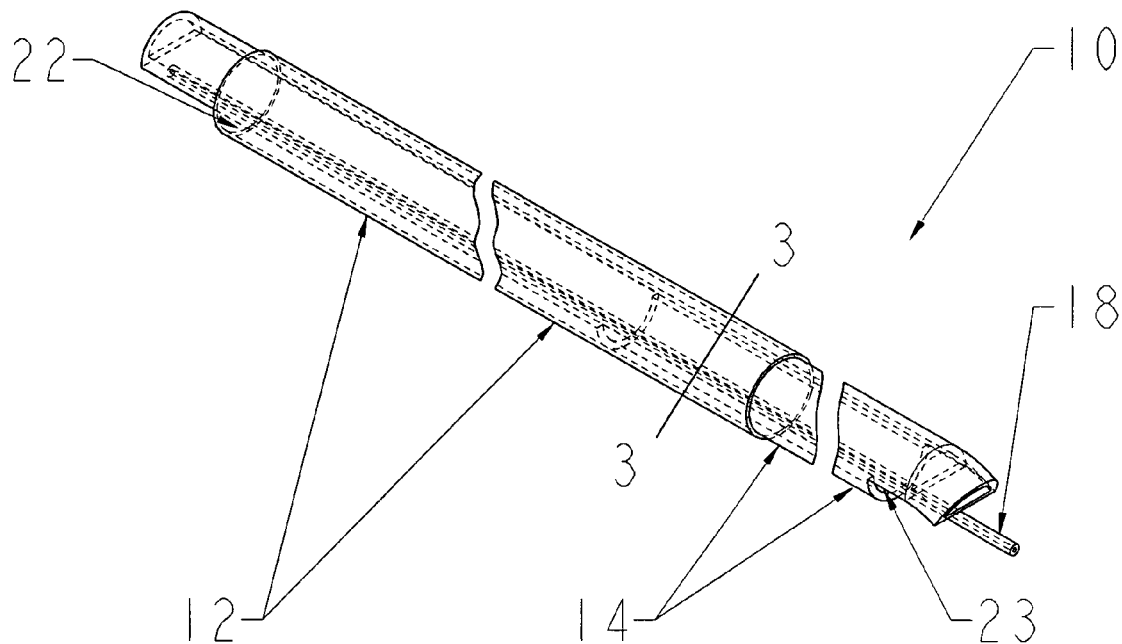
Figure 3B:
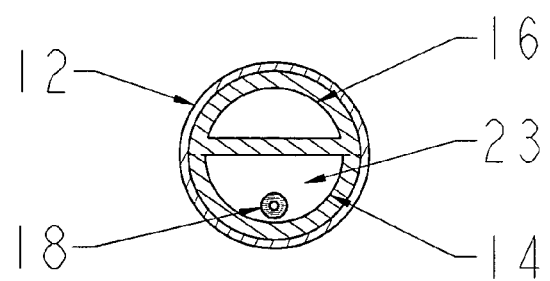
FIG. 3b is a cross-sectional schematic views of the assembly of FIG. 3a taken at section 3'-3'.

FIGS. 3a and b depict an alternate embodiment of the assembly 10, wherein the assembly further comprises a guide wire 18, which is arranged through a contiguous channel formed by the combination of the first catheter channel 22 and the catheter extension channel 23. The first catheter 12 and the catheter extension 14 may travel along the guidewire 18 in order to reach the area of the vasculature to be treated. Once at the affected area, the guide wire 18 may be left in place. As specifically shown in FIG. 3b, the guide wire 18 is arranged through the catheter extension channel 23.

Figure 4A:
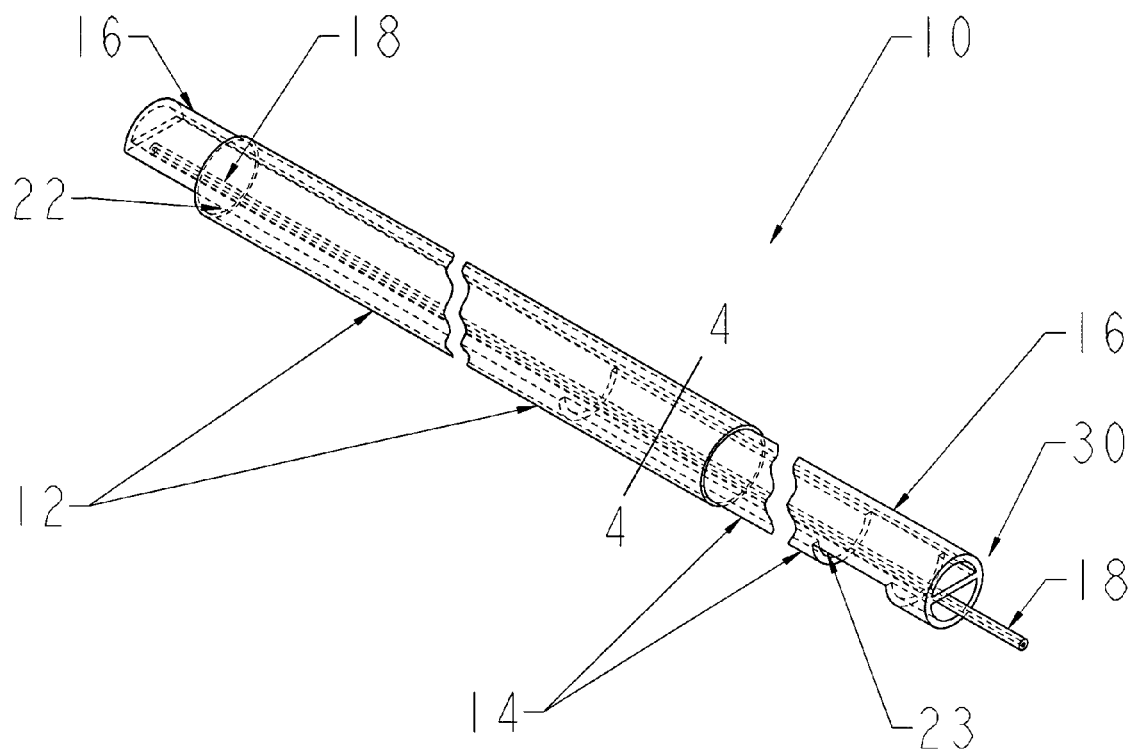
Figure 4B:
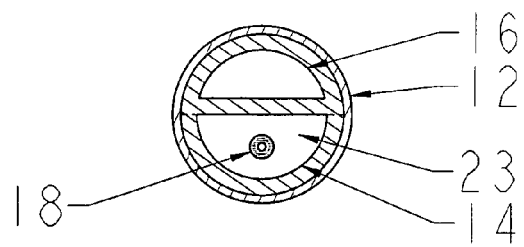
FIG. 4b is a cross-sectional schematic views of the assembly of FIG. 4a taken at section 4'-4'.

Another alternate arrangement for the passage of a guidewire through the assembly is shown by FIGS. 4a and 4b, wherein the guide wire 18 is arranged through a contiguous channel formed by the combination of the first catheter channel 22 and the catheter extension channel 23 as described earlier, and the guide wire 18 is further arranged to pass through the control member distal end 30. In this manner, the assembly may be slidably directed along the guidewire 18, wherein the control member distal end 30, as well as the contiguous channel will slidably follow the bends of the guidewire 18. As specifically shown in FIG. 4b, the guide wire 18 is arranged through the catheter extension channel 23.

Figure 5A:
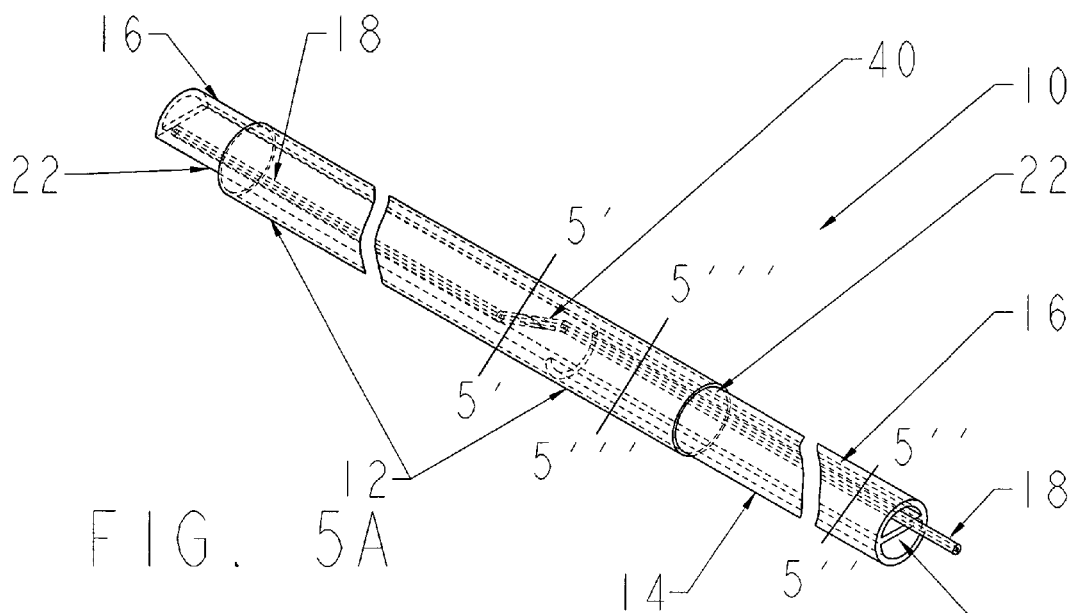
Figure 5B:
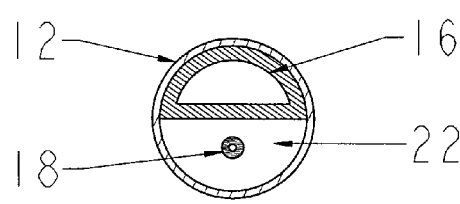
FIGS. 5b, 5c and 5d are cross-sectional schematic views of the assembly of FIG. 5a taken at sections 5'-5', 5"-5" and 5"'-5"', respectively.
Figure 5D:
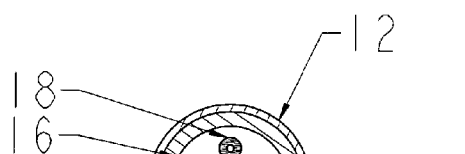
Figure 5C:
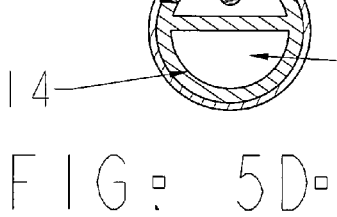

Yet another alternate arrangement of the assembly is depicted by FIGS. 5a, 5b and 5c, wherein the guidewire 18 is arranged so that at least a portion of both the first catheter channel 22 and the interior lumen of the control member 16 entrain the guide wire. The guidewire 18 is directed through an interface 40 located between the first catheter channel 22 and the lumen of the control member 16. The interface 40 functions as an opening designed to facilitate the passage of the guidewire 18 therethrough, and at the same time prevent leakage or fluid exchange between the infusate pathway and the extraction pathway. As specifically shown in FIG. 5b, the first catheter channel 22 and not the lumen of the control member 16 acts as a passageway for the portion of the guidewire 18 proximal to the interface 40. Distal to interface 40, the lumen of the control member 16 serves as a passageway for the portion of the guidewire 18, as illustrated in cross-section in FIGS. 5c and 5d. This arrangement of the assembly 10 prevents the guidewire 18 from traversing and partially occluding the narrower catheter extension channel 23. In this manner the cross-sectional area of the catheter extension channel 23 devoted to aspiration of debris is maximized, thereby minimizing the opportunity for cavitation or blockage. As the extraction pathway portion defined by the first catheter channel 22 is larger in diameter and cross-sectional area than that of the catheter extension channel 23, the guidewire may be arranged through the first catheter channel 22 with out significantly affecting the likelihood of cavitation, as the most restricted portion would be in the catheter extension channel 23.

Figure 6A:
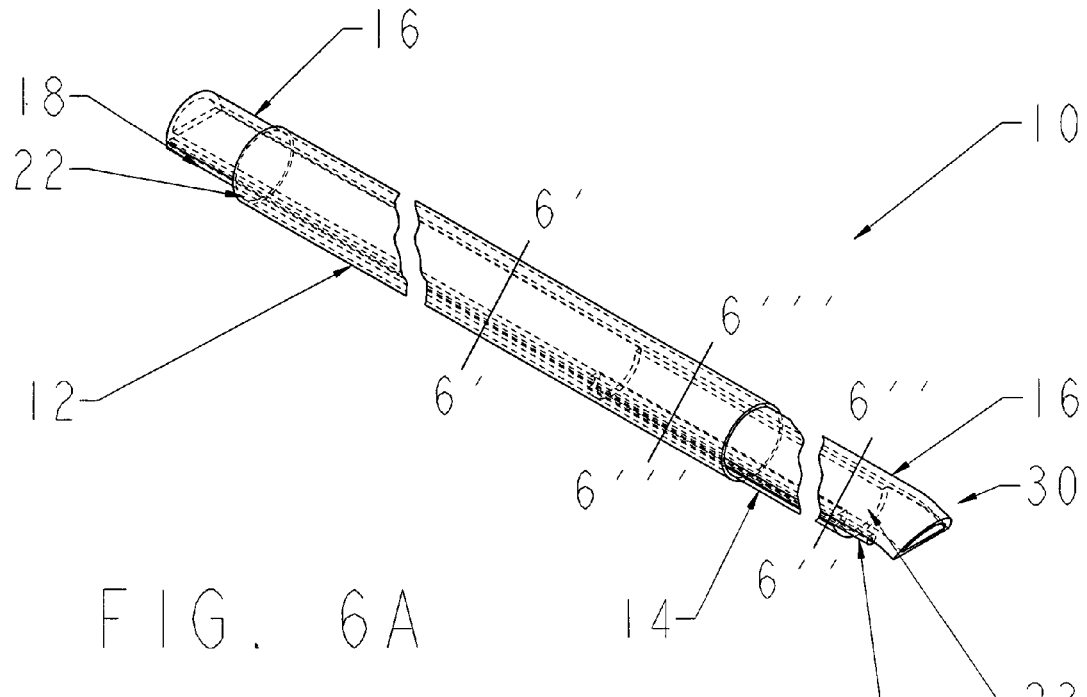
Figure 6B:
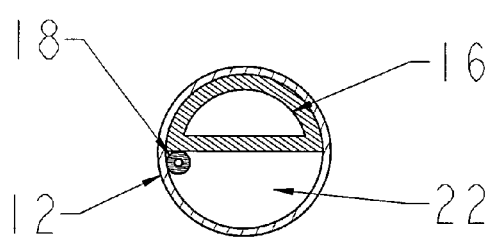
FIGS. 6b, 6c and 6d are cross-sectional schematic views of the assembly of FIG. 6a taken at sections 6'-6', 6"-6" and 6"'-6"', respectively.
Figure 6C:
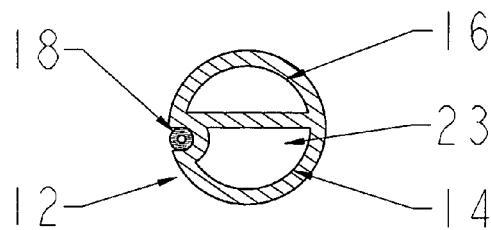
Figure 6D:
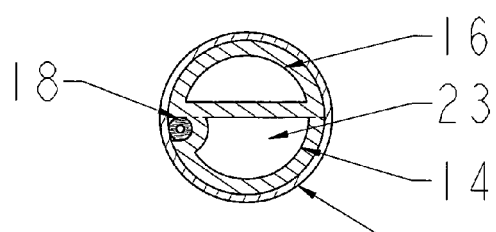

Still another alternative embodiment of the invention is depicted in FIG. 6a-6d, wherein the assembly 10 is depicted with the guidewire 18 arranged to pass through the first catheter channel 22. In this embodiment, the catheter extension channel 23 is completely open for the aspiration of debris, thereby maximizing the cross-sectional area available for aspiration, and serving to minimize the potential for cavitation or occlusion of the aspiration pathway. As depicted in FIGS. 6b, 6c and 6d, the catheter extension channel 23 is unobstructed by any part of the device and the region of the assembly 10 that is distal to the first catheter's distal end 26 may be moved independently of the guide wire 18. These three Figures also show that the guidewire 18 is outside of the lumen of the control member 16. It is recognized that further arranging the guidewire 18 to pass through the control member distal end 30 may serve to enable the portion of the assembly 10 that is distal to the first catheter's distal end 26 to be directed by the guidewire 18, without the side effect of reducing the cross-sectional area of the catheter extension channel 23 devoted to extraction.

Figure 7A:
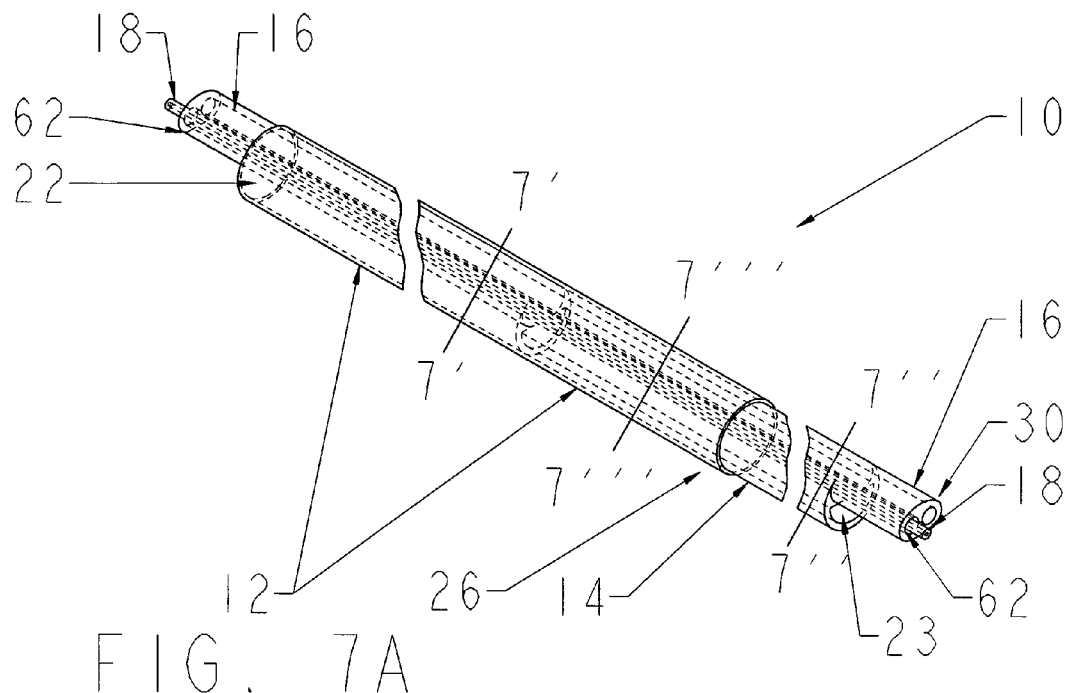
Figure 7B:
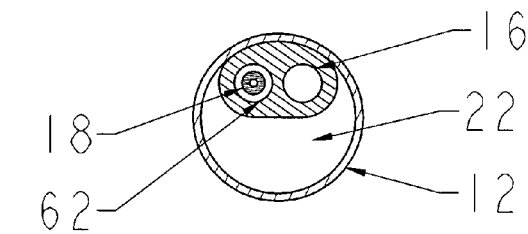
FIGS. 7b, 7c and 7d are cross-sectional schematic views of the assembly of FIG. 7a taken at sections 7'-7', 7"-7" and 7"'-7"', respectively.
Figure 7D:
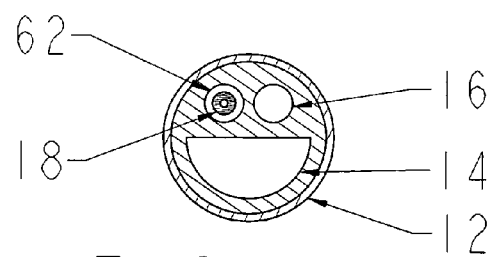
Figure 7C:
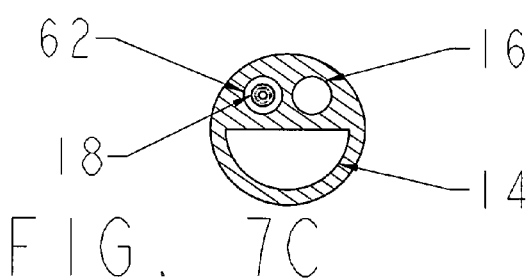

FIGS. 7a-7d depict another alternate embodiment of the invention, wherein the assembly 10, further comprises a third lumen 62 through which the guidewire 18 passes (see FIGS. 7b, 7c and 7d). This third lumen 62 extending at least the length of the first catheter channel 22, and further extending distally from the first catheter 12, alongside the catheter extension 14, and not within the catheter extension channel 23, as illustrated specifically in FIGS. 7c and 7d. As in the previous embodiment of FIG. 6, the aspiration through the catheter extension channel 23 is completely dedicated for the aspiration of debris, thereby maximizing the cross-sectional area available for aspiration, and serving to minimize the potential for cavitation or occlusion of the aspiration pathway. In order to prevent independent movement of the portion of the assembly distal to the first catheter's distal end 26, it is recognized (and as shown in FIG. 7a) that the catheter extension 14 may be slidably locked onto the guidewire 18, by arranging for the guidewire 18 and the third lumen 62 entraining the guide wire 18, attached to at least the control member's distal end 30. Alternatively, the third lumen 62 and the guidewire 18 may pass through and be slidably attached at the control member distal end (similarly depicted in FIG. 4a). In this manner, when a pushing force is exerted upon the control member 16 by the user, the force will be transmitted by the control member 16 to the catheter extension 14, which upon extension from the first catheter 12, would follow the tract established by the guide wire 18.

In each of the above embodiments, the first catheter 12 houses each of the other components of the assembly 10, and this is specifically illustrated in the cross-sectional views of FIGS. 3b, 4b, 5d, 6d, and 7d.

As a safety measure, steps may be taken to prevent the overextension of the catheter extension out from the distal end of the first catheter. These steps may include the addition of a flange (not shown) on the control member arranged to prevent the operator from pushing the control member excessively, as a flange larger than the opening of the first catheter would not be able to be inserted therein. Alternatively, visual markings may be applied to the control member, serving as a visual indicator at which point the catheter extension might be over extended and protruding out from the first catheter.

FIGS. 8a, b, and c depict various possible embodiments of the distal end of the control member, wherein the control member extends beyond the distal end of the catheter extension and serves to deliver infusate fluid. FIG. 8a depicts the control member 16 as having a distal opening 32 at the control member distal end 30, wherein the infusate fluid will flowably exit the opening 32 as a stream in a coaxial and distal direction. With this arrangement, the exiting stream may serve to blast through an occlusion in the vessel, by ablating the material creating the partial or complete blockage. With a lower rate of infusate delivery, the area may be more gently washed by the infusate in order to clear any debris created during the procedure. Alternatively, FIG. 8b depicts the control member 16 as having a plurality of radial openings 34, located at the control member distal end 30. The radial openings serve to direct the streams of infusate outwards from the control member 16, and against the vessel wall, in order to ablate or disturb any material causing a partial blockage of the vessel. FIG. 8c depicts an arrangement wherein the control member 16 incorporates a curve at the control member distal end 30, such that a radial opening 34 will, as a result of the curve, direct a stream coaxially, or nearly so, and in a proximal direction, such that fluid flow stream is towards the catheter extension distal end 28. In this manner, the infusate fluid along with any debris entrained within will be directed towards catheter extension 14 to be drawn into the extraction pathway for removal from the body.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes that come within the meaning and range of equivalency of the claims are intended to be embraced therein.

The invention claimed is:

1. A system for accessing lumens in living beings for the facilitation of intraluminal medical procedures, said system comprising a first catheter, a catheter extension, and a control member;
   wherein said catheter extension comprises a proximal end;
   wherein said control member is attached to at least the proximal end of said catheter extension and extending proximally therefrom;
   wherein said catheter extension is slidably arranged within said first catheter, and further wherein said catheter extension and said first catheter together define a contiguous channel for aspiration of at least one of fluid and debris from said living beings;
   wherein said contiguous aspiration channel that is defined by said first catheter is of a larger cross-sectional area than said contiguous aspiration channel defined by said catheter extension; and
   wherein said catheter extension has a length that is less than that of said first catheter.

2. The system of claim 1, wherein said catheter extension is of tubular form and further comprises a distal end, with said proximal end having an outside diameter being larger than the outside diameter of said distal end.

3. The system of claim 2, wherein said extension channel in said catheter extension is larger at said proximal end than at said distal end.

4. The system of claim 1, wherein said control member comprises a guide-wire passageway arranged between its proximal and distal ends to slidably accept a guide-wire.

5. The system of claim 4, wherein said guide-wire comprises a distal protection balloon.

6. The system of claim 1, wherein said control member comprises a fluid passageway arranged between its proximal and distal ends, with said fluid passageway arranged such that a fluid may be introduced at said proximal end and may exit said fluid passageway at said distal end.

7. The system of claim 6, wherein said fluid comprises infusate, saline, contrast media, drugs, biologically active agents, or any combinations thereof.

8. The system of claim 6, wherein said control member further comprises a guide-wire passageway arranged between its proximal and distal ends to slidably accept a guide-wire.

9. The system of claim 6, wherein said contiguous channel is attached to a vacuum source wherein said contiguous channel serves to remove said fluid together with any debris which may be created during said procedure.

10. The system of claim 6, wherein said introduction of said fluid is at a first flow rate and said removal of said fluid together with any debris is performed at a second and higher flow rate.

11. The system of claim 6, wherein said fluid passageway is arranged to introduce said fluid in the form of fluid jets.

12. The system of claim 11, wherein said fluid jets are directed radially from said distal end of said fluid passageway.

13. The system of claim 11, wherein said fluid jets are arranged to be introduced coaxially with said catheter extension, and directed into said extension channel therein.

14. The system of claim 1, wherein said contiguous channel comprises a guide-wire passageway arranged to slidably accept a guide-wire.

15. The system of claim 14, wherein said distal end of said control member is arranged to slidably accept said guide-wire.

16. The system of claim 1, wherein said channel of said first catheter comprises a guide-wire passageway arranged to slidably accept a guide-wire, and further wherein said extension channel of said catheter extension does not comprise said guide wire passageway.

17. The system of claim 1, further comprising a third lumen, said third lumen having a proximal end and a distal end, with said third lumen extending through the channel in said first catheter from at least said distal end to at least said proximal end, said third lumen being arranged to slidably accept a guide wire.

18. A system for accessing lumens in living beings for the facilitation of intraluminal medical procedures, said system comprising a first catheter, a catheter extension, a guidewire, and a control member;

(a) wherein said first catheter has a proximal end and a distal end with a channel therebetween, and being arranged to slidably and telescopically accept said catheter extension in said channel with said catheter extension, thereby creating an overlapping segment, (b) wherein said catheter extension comprises a proximal end and a distal end with an extension channel therebetween, with said channel and said extension channel operating together to form a contiguous channel, further wherein said guidewire passes through at least a portion of said first catheter but does not pass through said extension channel, and (c) wherein said control member has a proximal and a distal end with an elongate body arranged therebetween, and with said control member being attached to at least the proximal end of said catheter extension, and said elongate body of said control member extending at least to the proximal end of said first catheter, with said control member being arranged to cause axial movement of said catheter extension with respect to said first catheter in response to an application of axial force at the proximal end of said control member.

19. A system for accessing lumens in living beings for the facilitation of intraluminal medical procedures, said system comprising a first catheter, a catheter extension, and a control member;

(a) wherein said first catheter has a proximal end and a distal end with a channel therebetween, and being arranged to slidably and telescopically accept said catheter extension in said channel with said catheter extension, thereby creating an overlapping segment, (b) wherein said catheter extension comprises a proximal end and a distal end with an extension channel therebetween, with said channel and said extension channel operating together to form a contiguous channel, said contiguous channel being arranged for bi-directional flow of infusate fluid into, and aspirate fluid out of, said living beings, and (c) wherein said control member has a proximal and a distal end with said distal end of said control member being attached to said catheter extension, and said proximal end of said control member extending at least to the proximal end of said first catheter, with said control member being arranged to cause said catheter extension to be at least partially retracted into said channel in said first catheter upon the application of an axial pulling force at the proximal end of said control member.

20. The system of claim 19, further wherein said control member is arranged to cause said catheter extension to rotate in said first catheter upon the application of a twisting force at the proximal end of said control member.

21. The system of claim 1, wherein said control member comprises a lumen from its proximal end to a plurality of openings at or near its distal end.

22. The system of claim 21, wherein said control member is arranged to deliver infusate fluid.

23. The system of claim 19, wherein said control member comprises a lumen from its proximal end to a plurality of openings at or near its distal end.

24. The system of claim 23, wherein said control member is arranged to deliver infusate fluid.

25. The system of claim 24, wherein said first catheter channel is arranged to aspirate fluid from said living beings.

26. The system of claim 19, wherein said extension channel has a length that is less than that of said channel.

27. The system of claim 1, arranged for infusion and aspiration of fluid.

28. The system of claim 1, wherein said control member has a proximal end and a distal end with an elongate body arranged therebetween, and with said control member being attached to at least the proximal end of said catheter extension, and said elongate body of said control member extending at least to the proximal end of said first catheter, with said control member being arranged to cause axial movement of said catheter extension with respect to said first catheter in response to an application of axial force at the proximal end of said control member.

* * * * *